(12) United States Patent
Chan et al.

(10) Patent No.: US 6,500,184 B1
(45) Date of Patent: Dec. 31, 2002

(54) SUTURING APPARATUS AND METHOD OF SUTURING

(76) Inventors: Yung C. Chan, 2938 Old Baltimore Rd., Draper, VA (US) 24324; Mei H. Chan, 2938 Old Baltimore Rd., Draper, VA (US) 24324; King H. Chan, 2938 Old Baltimore Rd., Draper, VA (US) 24324; Ming H. Chan, 2938 Old Baltimore Rd., Draper, VA (US) 24324

( * ) Notice: Subject to any disclaimer, the term of this patent is extended or adjusted under 35 U.S.C. 154(b) by 0 days.

(21) Appl. No.: 09/774,083

(22) Filed: Jan. 31, 2001

(51) Int. Cl.[7] .............................. A61B 17/04
(52) U.S. Cl. ................. 606/144; 606/148; 606/232
(58) Field of Search ................ 606/144, 148, 606/232

(56) References Cited

U.S. PATENT DOCUMENTS

| | | | | |
|---|---|---|---|---|
| RE340,210 | * | 8/1992 | Mueller et al. ............. | 604/533 |
| 5,224,946 A | * | 7/1993 | Hayhurst et al. ............ | 606/144 |
| 5,354,298 A | * | 10/1994 | Lee et al. .................... | 606/139 |
| 5,391,182 A | * | 2/1995 | Chin .......................... | 128/898 |
| 5,417,691 A | * | 5/1995 | Hayhurst ..................... | 606/144 |
| 5,470,337 A | * | 11/1995 | Moss .......................... | 606/139 |
| 5,507,755 A | * | 4/1996 | Gesl et al. ................... | 606/139 |
| 5,562,685 A | * | 10/1996 | Mollenauer et al. ........ | 112/169 |
| 5,575,801 A | * | 11/1996 | Habermeyer et al. ....... | 606/148 |
| 5,601,571 A | * | 2/1997 | Moss .......................... | 606/139 |
| 5,626,614 A | * | 5/1997 | Hart ............................ | 606/232 |
| 5,800,445 A | * | 9/1998 | Ratcliff et al. .............. | 606/116 |
| 5,997,554 A | * | 12/1999 | Thompson ................... | 606/148 |
| 6,056,760 A | * | 5/2000 | Koike et al. ................ | 606/139 |
| 6,066,146 A | * | 5/2000 | Carroll et al. .............. | 606/144 |
| 6,306,159 B1 | * | 10/2001 | Schwartz et al. ........... | 606/148 |
| 2001/0041916 A1 | * | 11/2001 | Bonutti ....................... | 606/232 |

* cited by examiner

Primary Examiner—Rodney M. Lindsey
(74) Attorney, Agent, or Firm—William L. Klima

(57) ABSTRACT

The present invention is directed to an apparatus for suturing a deep incision or wound through the abdominal fascia on an animal or human, and method of suturing.

21 Claims, 4 Drawing Sheets

SUTURING APPARATUS AND METHOD OF SUTURING

FIELD OF THE INVENTION

The present invention is directed to an apparatus for suturing a deep incision or wound on an animal or human, and method of suturing.

BACKGROUND OF THE INVENTION

The present invention relates to the suturing of a deep incision or wound during a medical procedure.

In many cases, at the end of a routine laparoscopy procedure, the closure of the umbilicus stab wound creates a difficult task for the surgeon. It is important to properly close this umbilicus stab wound otherwise a hernia may result. To suture close this type of wound sometimes is very difficult, especially with very obese patients.

Normally, the sutures used include a silk thread attached to the end of a needle. To push the needle through an obese deep abdominal defect, one has to push the needle hard. However, the needle can break or bend creating complications during the surgery. To recover a broken needle through the wound is a difficult task because of the depth of the wound and the lack of visibility.

Thus, the present invention attempts to solve these problems.

SUMMARY OF THE INVENTION

A first object of the present invention is to provide an improved suturing apparatus.

A second object of the present invention is to provide an improved suturing apparatus including a hollow needle device provided with a suture delivery passageway, the hollow needle device including a cutting tip at one end and a gripping portion at an opposite end thereof, a suture loading device provided with a loop portion, the loop portion of the loading device configured to be inserted through the needle so that the loop portion extends beyond the cutting tip of the needle whereby a suture can be threaded through the loop portion and then the loading device can be withdrawn from the needle to load the suture within the suture delivery passageway of the hollow needle device readied for insertion through the tissue surrounding the deep incision or wound, and a plunger device configured to force the loaded suture disposed within the suture delivery passageway of the hollow needle device out of the cutting tip penetrating the abdominal fascia and into the peritoneal cavity.

A third object of the present invention is to provide a suturing apparatus wherein the gripping portion is a radially extending gripping portion.

A fourth object of the present invention is to provide a suturing apparatus wherein the radially extending gripping portion is defined by a circular plate connected at one end of the hollow needle device.

A fifth object of the present invention is to provide a suturing apparatus wherein the cutting tip of the hollow needle device is a beveled tip.

A sixth object of the present invention is to provide a suturing apparatus wherein the suture loading device includes a plunger portion connected to said loop portion.

A seventh object of the present invention is to provide a suturing apparatus wherein the plunger portion of the suture loading device is provided with a gripping portion.

A eighth object of the present invention is to provide a suturing apparatus wherein the gripping portion of the suture loading device is a paddle-shaped gripping portion.

A ninth object of the present invention is to provide a suturing apparatus wherein the suturing apparatus includes a suture provided with an anchoring device, the suture being configured to be inserted through the suture delivery passageway of the needle.

A tenth object of the present invention is to provide a suturing apparatus wherein the anchoring device is an oblong-shaped anchoring device connected to the suture.

An eleventh object of the present invention is to provide a suturing apparatus wherein the oblong-shaped anchoring device is connected to the suturing line of the suturing device in a manner to allow the oblong-shaped anchoring device to be aligned with a length of the suturing device when loaded within the suturing device delivery passageway of the hollow needle device, and then align transversely relative to the length of the suturing device after insertion through the abdominal fascia and into the peritoneal cavity.

A twelfth object of the present invention is to provide a suturing apparatus wherein the oblong-shaped anchoring device is provided with a through hole to allow the suturing line of the suturing device to pass therethrough for connecting the suturing line to the oblong-shaped anchoring device.

A thirteenth object of the present invention is to provide a suturing apparatus wherein the suturing device is provided with an additional anchoring device.

A fourteenth object of the present invention is to provide a suturing apparatus wherein the anchoring devices are set apart a predetermined distance so that one anchoring device is embedded on one side of the deep incision or wound through the abdominal fascia and the other anchoring device is embedded on an opposite side of the deep incision or wound through the abdominal fascia.

A fifteenth object of the present invention is to provide a suturing apparatus wherein the anchoring devices are plate-shaped anchoring devices connected to the suturing line of the suturing device.

A sixteenth object of the present invention is to provide a suturing apparatus wherein the oblong-shaped anchoring devices are oblong-shaped anchoring devices connected to the suturing device in a manner to allow the oblong-shaped anchoring devices to be aligned with a length of the suturing device when loaded within the suturing device delivery passageway of the hollow needle device, and then align transversely relative to the length of the suturing device after insertion through the abdominal fascia into the peritoneal cavity.

A seventeenth object of the present invention is to provide a suturing apparatus wherein the oblong-shaped anchoring device is a rod-shaped anchoring device connected to the suturing device.

An eighteenth object of the present invention is to provide a suturing apparatus wherein the rod-shaped anchoring device is provided with a throughhole for connecting with the suturing device.

A nineteenth object of the present invention is to provide a suturing apparatus wherein the rod-shaped anchoring device is provided with at least one groove for accommodating the suturing line of the suturing device when said rod-shaped anchoring device is aligned with a length of the suturing device.

A twentieth object of the present invention is to provide a method of suturing a deep incision or wound through the abdominal fascia, the method comprising the steps of making a set of penetrating holes on opposites sides of the deep incision or wound with a hollow needle device, inserting a suturing device through each penetrating hole in the tissue, anchoring the suturing device in the holes in the tissue, and tightening the suturing device to pull the penetrating holes in the tissue together to close the deep incision or wound.

A twenty-first object of the present invention is a method of suturing a deep incision or wound through the abdominal fascia, the method comprising the steps of making a set of penetrating holes on opposites sides of the deep incision or wound with a hollow needle device, inserting separate suturing devices through each penetrating hole in the tissue, anchoring the suturing devices in the penetrating holes in the tissue, and tying the suturing devices together to pull the penetrating holes in the tissue together to close the deep incision or wound.

The present invention is directed to a suturing apparatus and method of suturing. The suturing apparatus comprises three (3) separate components including 1) a hollow needle device; 2) a suture loading device; and 3) a plunger device. This suture apparatus in combination with a suturing device according to the present invention is utilized by a surgeon to close a deep incision or wound, particularly in an obese patient.

The suturing device according to the present invention includes a suturing line connected to at least one anchoring device. Specifically, a suturing line such as a silk thread or monofilament is provided with an anchoring device (e.g. plate-shaped, rod-shaped or other suitably shaped anchor to pass through a hole cut by the cutting tip portion of the hollow needle device, and then grip the surrounding abdominal fascia when the suturing device is pulled on). Thus, the anchoring device must be configured to pass through a hole cut by the cutting tip portion of the hollow needle device, however, configured not to pass through the same hole upon attempting to pull the anchoring device back through the same hole. Thus, the anchoring device is configured to pass through the hole in only one (1) way or one (1) direction.

The hollow needle device of the suturing apparatus according to the present invention is configured to receive the suturing line and anchoring device of the suturing device. Thus, the anchoring device must be configured (i.e. sized and shaped) to fit within the suturing device delivery passageway of the hollow needle device. A suture loading device provided with a loop portion is passed through the hollow needle device, and then the suturing line of the suturing device is threaded through the loop portion. The suture loading device is retracted to pull the suturing line of the suturing device and anchoring portion of the suturing device into the hollow needle device to load the suturing device within the hollow needle device readied for insertion through the abdominal fascia surrounding the deep incision or wound. After the suturing device is loaded within the hollow needle device, a plunger device is inserted into one end of the hollow needle device to force the suturing device through the suturing device delivery passageway of the hollow needle device out the cutting tip portion of the hollow needle device through the abdominal fascia that the hollow needle device has been already penetrated therethrough. The hollow needle device is removed leaving the anchoring device of the suture on the opposite side of the one (1) or more layers of tissue, securely anchoring the suturing device so that the suturing device can be tightened or tied to close the deep incision or wound.

DETAILED DESCRIPTION OF PREFERRED EMBODIMENT

Figure 1:
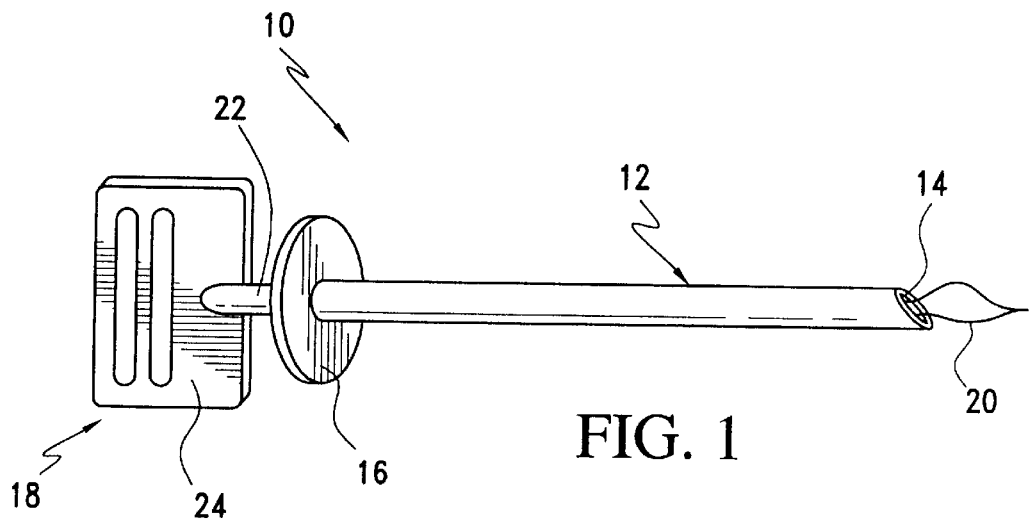
FIG. 1 is perspective view of a suturing apparatus according to the present invention assembled and ready to load a suturing device according to the present invention.
Figure 2:
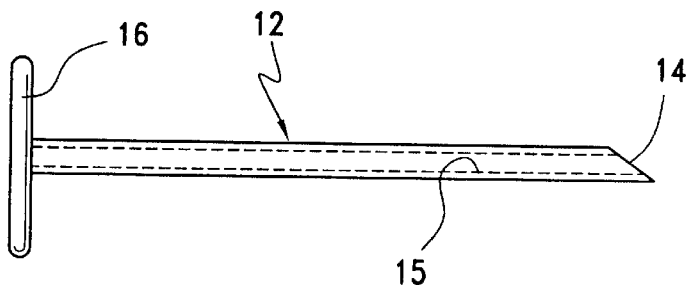
FIG. 2 is a side elevational view of the hollow needle portion of the suturing apparatus shown in FIG. 1.

A suturing apparatus 10 according to the present invention is shown in FIG. 1. The suturing apparatus 10 includes 1) a hollow needle device 12 including a cutting tip portion 14, suture delivery passageway 15, and gripping portion 16; and 2) a separate suture loading device 18. The suture loading device 18 includes a loop portion 20 connected to a plunger portion 22, which is connected to a gripping portion 24.

Figure 4:
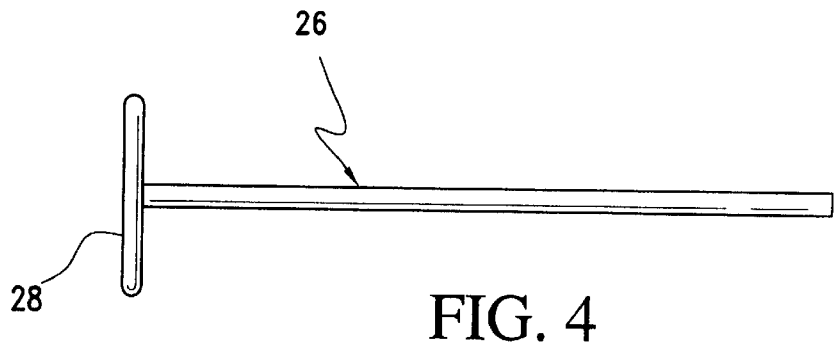
FIG. 4 is a side elevational view of a plunger device to be used with the suturing apparatus shown in FIG. 1 after a suture has been loaded within the hollow needle and the suture loading device has been removed therefrom.

More specifically, the hollow needle portion 12 includes a cutting tip portion 14 (e.g. beveled and sharpened tip) configured to cut through or penetrate the abdominal fascia surrounding the deep incision or wound. The lumen through the hollow needle portion 12 defines a suturing device delivery passageway 15 into which the suturing device according to the present invention is loaded readied for insertion through the abdominal fascia. The hollow needle device 12 is also provided with a gripping portion 16 to provide a finger grip when the suturing device according to the present invention is being forced through the suturing device delivery passageway 15 by the plunger device 26, as shown in FIG. 4. The hollow needle device 12 can be made of metal, ceramic, or plastic, or combination thereof.

Figure 3:
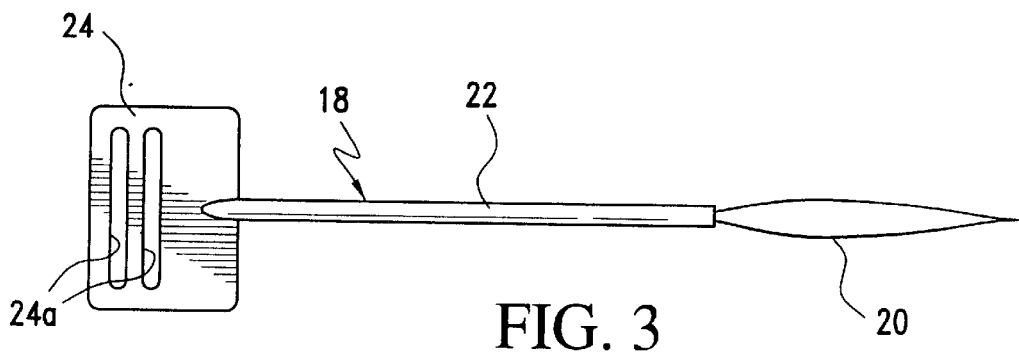
FIG. 3 is a side elevational view of the suture loading device of the suturing apparatus shown in FIG. 1.

The suture loading device 18 is shown in FIG. 3. The suture loading device 18 includes a loop portion 20 (e.g. a pair of wires imbedded within one (1) end of the plunger 22 and connected together at an opposite end or a single piece of wire bent in half with the ends imbedded in the plunger 22). The gripping portion 24 is provided with a pair of grooves 24a provided in the surface thereof to enhance the gripping ability of the gripping portion 24, for example, between a thumb and forefinger of the surgeon for inserting and withdrawing the suture loading device 18 into and out of the hollow needle device 12. The suture loading device 18 can be made of metal, ceramic, or plastic, or combination thereof.

Figure 5:
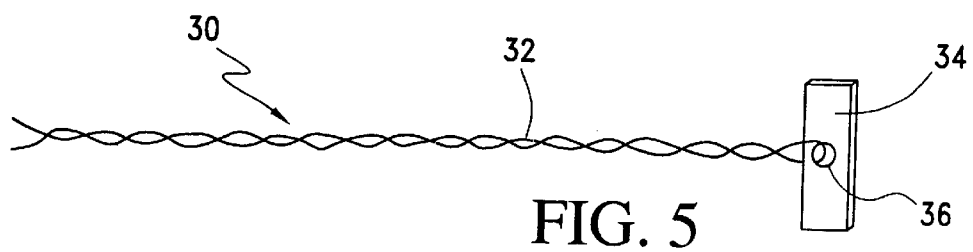
FIG. 5 is a side elevational view of a suture according to the present invention with a plate-shaped anchoring portion.

As shown in FIG. 4, a plunger device 26 provided with a gripping portion 28 is configured to be inserted within the hollow needle device 12 after a suture according to the present invention has been loaded within the hollow needle device 12 of the suturing apparatus 10. The plunger device 26 can be made of metal, ceramic, or plastic, or combination thereof A suturing device 30 according to the present invention is shown in FIG. 5. The suturing device includes a suturing line 32 (e.g. strands, woven or monofilament) provided with an oblong plate-shaped anchoring device 34. The oblong plate-shaped anchoring device 34 is provided with a throughole 36 through which the suturing line 32 is threaded therethrough to connect the oblong plate-shaped anchoring device 34 to the suturing line 32. The oblong plate-shaped anchoring device 34 shown in FIG. 5 is a preferably oblong plate-shaped anchoring device 34 capable of being rotated from one position (e.g. parallel to length of line portion 32 readied for insertion) to another position (e.g. transverse to length of line portion 32 readied for anchoring). During the insertion mode, the oblong plate-shaped anchoring device 34 is rotated to be aligned with the length of the suturing line 32, and once inserted through the abdominal fascia is rotated to a position transverse relative to the length of the line portion 32 shown in FIG. 5. In this manner, the oblong plate-shaped anchoring device 34 is allowed to be inserted through the hole in the tissue being cut and penetrated by the cutting tip portion 14 of the hollow needle device 12 and then rotated to prevent the oblong plate-shaped anchoring device 34 from being withdrawn from the puncture wound made by the hollow needle device 12.

Figure 6:
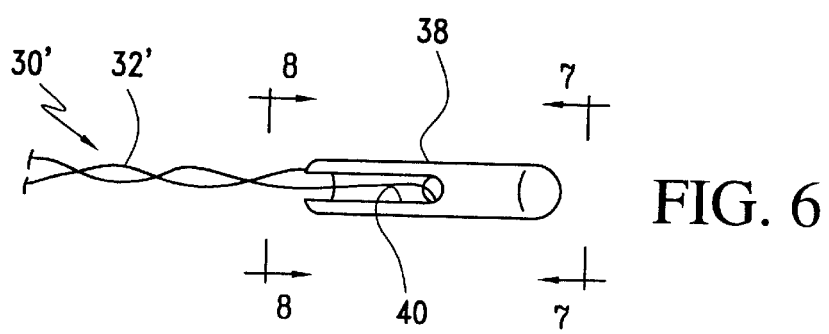
FIG. 6 is partial broken away side elevational view of a another suture according to the present invention provided with a rod-shaped anchoring portion.
Figure 7:
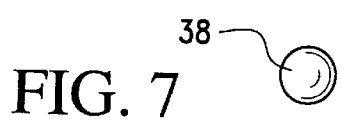
FIG. 7 is an end view of the rod-shaped anchoring device shown in FIG. 6.
Figure 8:
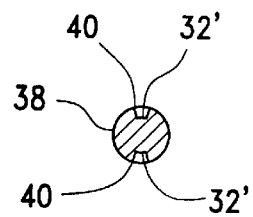
FIG. 8 is an opposite end view of the rod-shaped anchoring device shown in FIG. 6.

In an alternative embodiment, an oblong rod-shaped anchoring device 38 is substituted for the oblong plate-shaped anchoring device 34 shown in FIG. 5. The oblong rod-shaped anchoring device 38 is provided with a pair of grooves 40 located on either side of the rod-shaped anchoring device 38, and are partial length (e.g. shown extending approximately one-half (½) along the length of the rod-shaped anchoring device 38). In the operational mode shown in FIG. 6, the oblong rod-shaped anchoring device 38 is shown aligned with the length of the suturing line 32' so that the suturing line 32' is disposed within the grooves 40 to facilitate loading the suture 30' and oblong rod-shaped anchoring device 38 within the suturing device delivery passageway 15 of the hollow needle device 12. Once the oblong rod-shaped anchoring device 38 has been inserted through the abdominal fascia, the oblong rod-shaped anchoring device 38 is rotated to a transverse position relative to the length of the suture 30' or length of the suturing line 32' to provide anchoring to allow the deep incision or wound to be closed.

Figure 9:
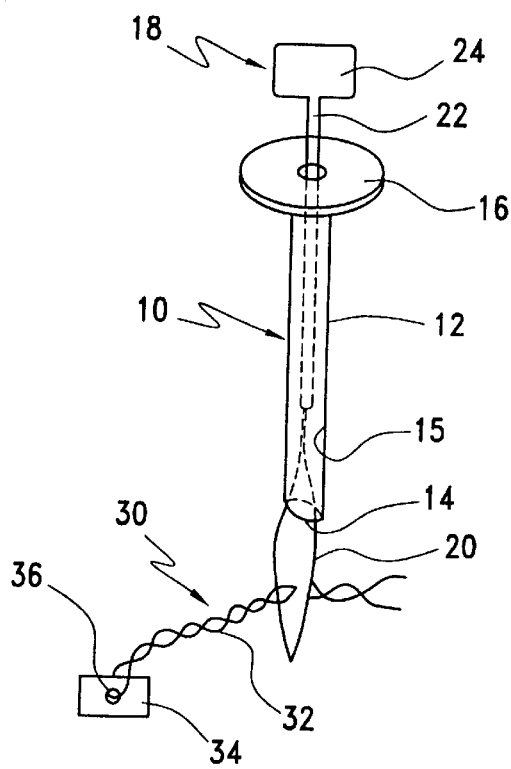
FIG. 9 is a diagrammatic view showing a suture being loaded into the suturing apparatus shown in FIG. 1.
Figure 10:
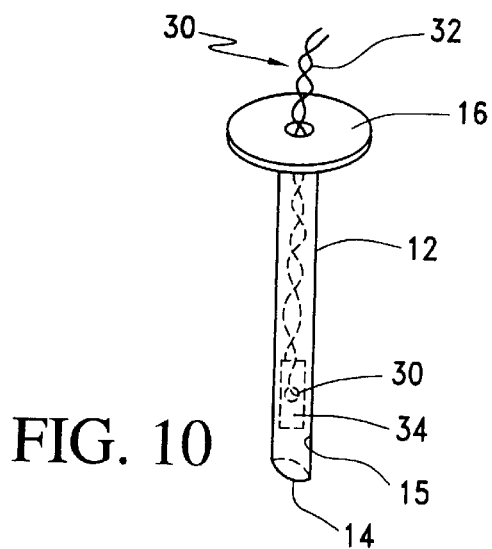
FIG. 10 is a diagrammatic view of a suture according to the present invention loaded into the hollow needle of the suturing apparatus shown in FIG. 1.
Figure 11:
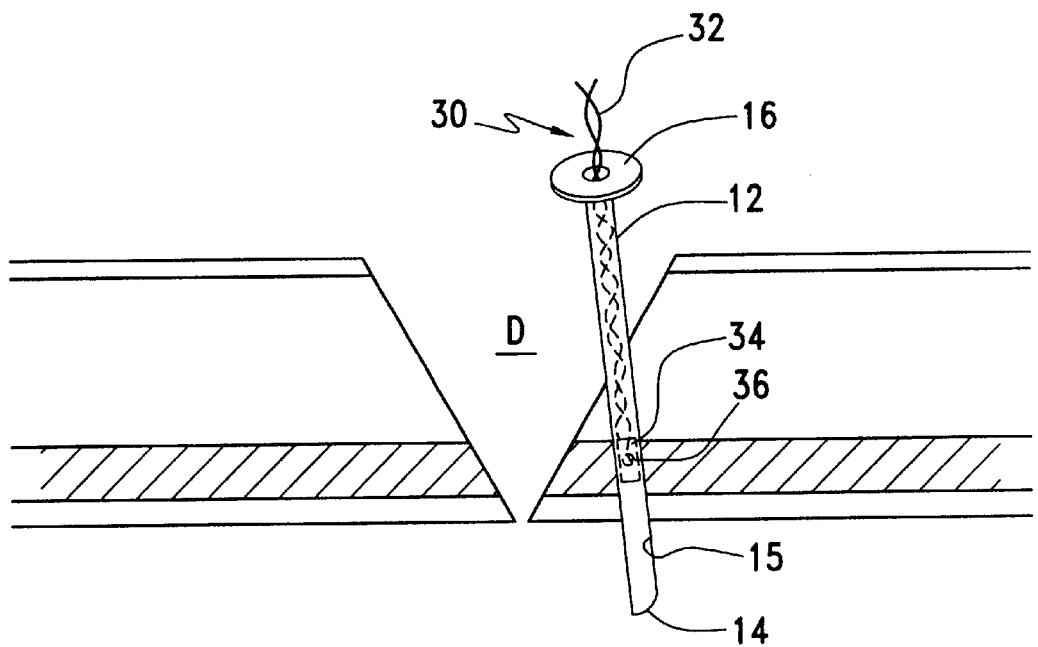
FIG. 11 is a diagrammatic view of the hollow needle loaded with a suture according to the present invention penetrating through a plurality of tissue layers adjacent a deep incision or wound.
Figure 12:
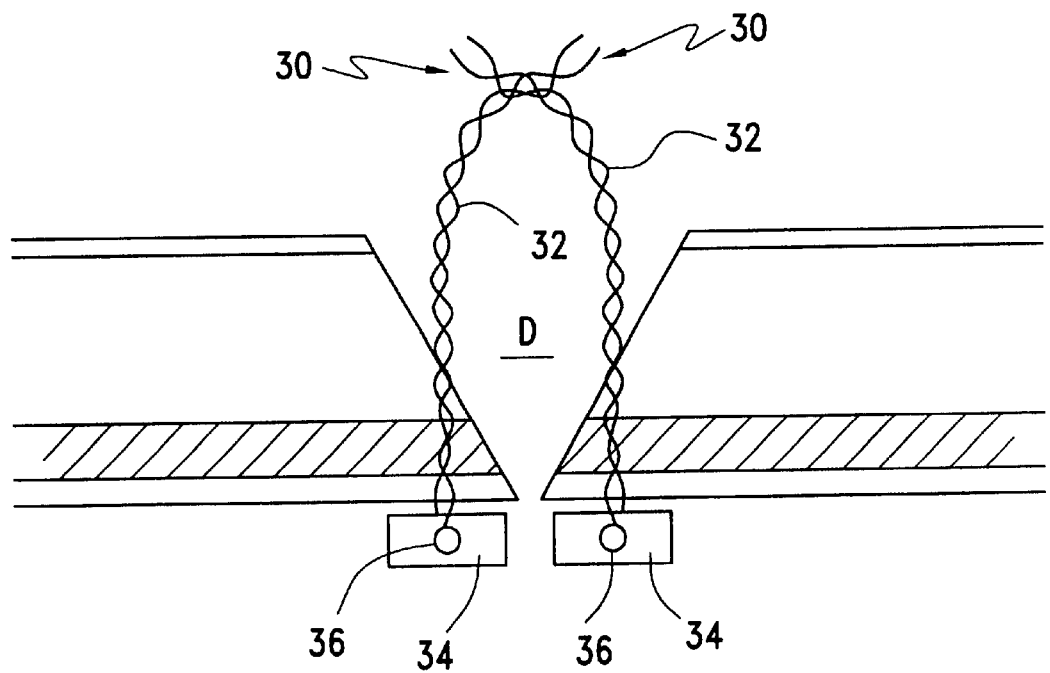
FIG. 12 is a diagrammatic view showing two (2) separate sutures according to the present invention inserted through either side of the deep incision or wound ready to be tied together to close the deep incision or wound.

As shown in FIG. 9, the suturing device 30 is loaded within the hollow needle device 12 by threading the suturing line 32 through the loop portion 20 of the suture loading device 18. A person grips the gripping portion 24 between his or her thumb and forefinger and retracts the suturing loading device 18 from the hollow needle device 12 pulling the suturing device 30 into the suturing device delivery passageway 15 of the hollow needle device 12. The suturing device 30 is loaded with the oblong plate-shaped anchoring device 34 leading the suturing line 32 in the direction of insertion of the suturing device 30 into the abdominal fascia surrounding the deep incision or wound. The cutting tip portion 14 of the hollow needle device 12 is forced through a plurality of layers of tissue adjacent the deep incision or wound so that the cutting tip portion 14 fully penetrating through the plural layers of tissue as shown in FIG. 11. The plunger device 26 shown in FIG. 4 is loaded into the open end of the hollow needle device 12 and pressed downwardly into contact with the oblong plate-shaped anchoring device 34 to begin forcing the suturing line 32 through the suturing device delivery passageway 15 of the hollow needle device 12. The plunger device 26 is pushed downwardly until the oblong plate-shaped anchoring device 34 exits the end of the cutting tip portion 14 of the hollow needle device 12, and then the hollow needle device 12 is retracted from the layers of tissue leaving the suturing device 30 in position as shown in FIG. 12. Upon pulling the suturing line 32 of the suturing device 30, the oblong plate-shaped anchoring device 34 rotates transversely relative to the length to the suturing device to anchor the suturing device 30 within the layers of tissue. As shown in FIG. 12, a pair of suturing devices 30 are provided on either side of the deep incision or wound. The suturing lines 32 of the suturing devices 30 are tied together to close the deep incision or wound.

Figure 13:
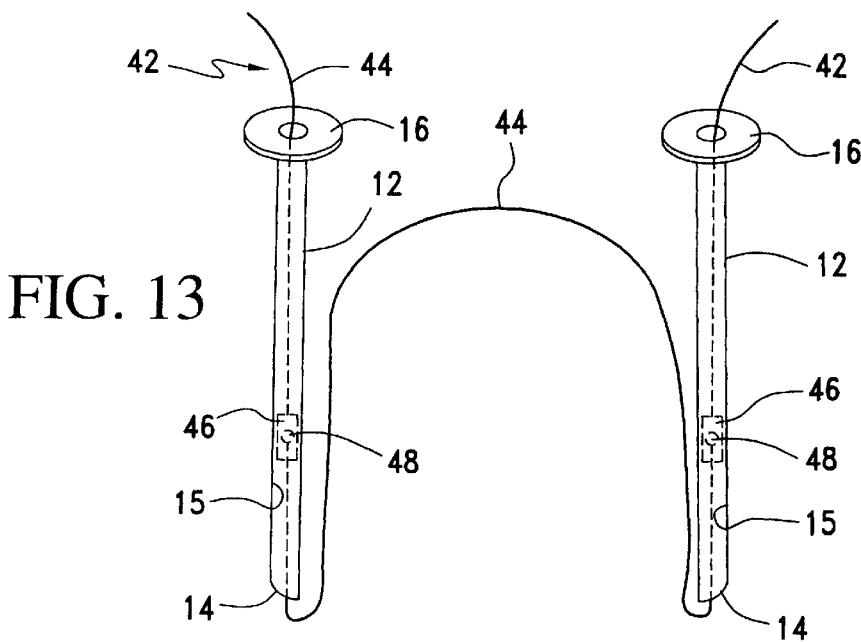
FIG. 13 is a diagrammatic view showing another suturing device according to the present invention having a pair of spaced apart anchoring devices loaded into two (2) separate hollow needle devices of suturing apparatus according to the present invention readied for insertion of the suturing devices.
Figure 14:
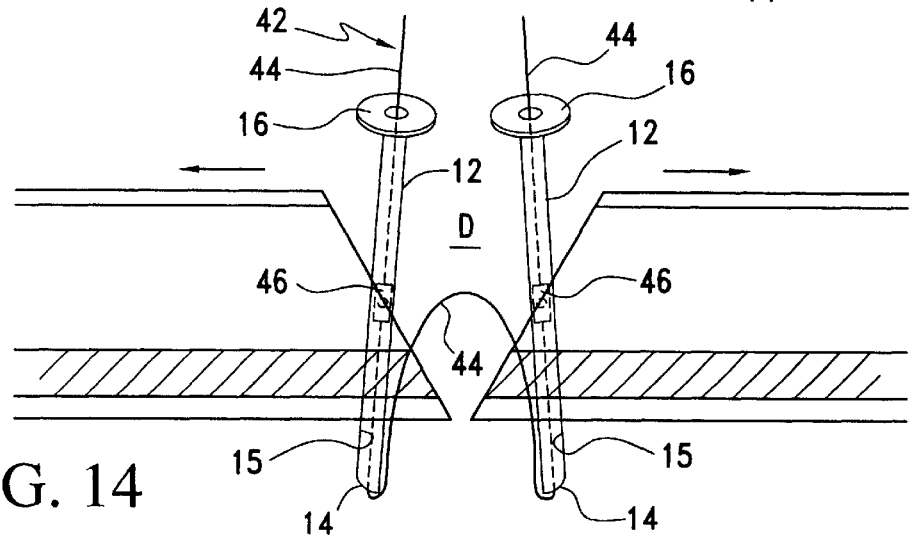
FIG. 14 is a diagrammatic view of the arrangement shown in FIG. 13 with each hollow needle devices penetrating through the abdominal fascia for insertion of the two (2) anchoring devices through the two (2) separate holes through the tissue layers.
Figure 15:
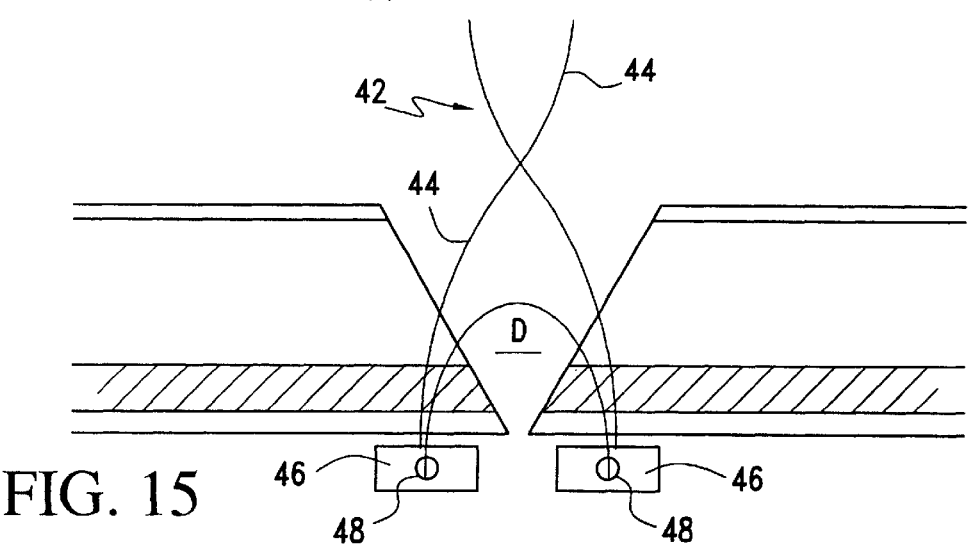
FIG. 15 is a diagrammatic view showing the suturing device with both anchoring devices properly installed readied for tightening the suturing device to close the deep incision or wound.

In an alternative embodiment, a suturing device 42 including a suturing line 44 is provided with a pair of spaced apart anchoring devices 46. The anchoring devices 46 are connected to the suturing line 44 by throughholes 48 extending through the anchoring devices 46. The suturing device 42 is loaded in a pair of hollow needle devices 12 with the anchoring devices 48 as shown in FIG. 13. The cutting tip portions 14 of the hollow needle devices 12 are inserted through the abdominal fascia as shown in FIG. 14. Both hollow needle devices 12 are withdrawn leaving the suturing device 42 in position and ready to be tightened as shown in FIG. 15.

What is claimed is:

1. A suturing apparatus configured for suturing tissue surrounding a deep incision or wound in the abdominal fascia, said apparatus comprising:

a hollow needle device provided with a suturing device passageway, said hollow needle device including a cutting tip at one end and a gripping portion at an opposite end thereof;

a plunger device configured to force a loaded suturing device disposed within said suturing device passageway out of said cutting tip portion of said hollow needle device after penetrating the tissue surrounding the deep incision or wound in the abdominal fascia; and a suturing device configured to be loaded into said hollow needle device and forced by said plunger device through said suturing device passageway to penetrate the tissue surrounding the deep incision or wound to at least partially close the deep incision or wound, said suturing device including multiple oblong-shaped anchoring devices each provided with a through-hole and a suture line passing through said through-holes of said anchoring device.

2. An apparatus according to claim 1, wherein said gripping portion of said hollow needle device is a radial extending gripping portion.

3. An apparatus according to claim 2, wherein said radial extending gripping portion is defined by a circular plate connected at one end of said hollow needle device.

4. An apparatus according to claim 1, wherein said cutting tip is a beveled tip.

5. An apparatus according to claim 1, wherein said suture loading device includes a plunger portion connected to said loop portion.

6. An apparatus according to claim 5, wherein said plunger portion is connected to a gripping portion.

7. An apparatus according to claim 6, wherein said gripping portion is a paddle-shaped gripping portion.

8. An apparatus according to claim 1, wherein said anchoring devices are located at different positions along a length of said suturing line.

9. An apparatus according to claim 8, wherein said anchoring devices are oblong-shaped anchoring devices connected to said suturing line of said suturing device.

10. An apparatus according to claim 9, wherein said anchoring devices are oblong-shaped anchoring devices connected to said suturing line of said suturing device in a manner to allow said oblong-shaped anchoring devices to be aligned with a length of said suturing device when loaded within said suturing device delivery passageway of said hollow needle device and then align transversely relative to said suturing device after insertion through the tissue surrounding the deep incision or wound to anchor said suturing device.

11. An apparatus according to claim 9, wherein said oblong-shaped anchoring devices are provided with a through hole to allow said suturing device to pass therethrough for connecting said suturing line of said suturing device to said oblong-shaped anchoring devices.

12. An apparatus according to claim 8, including at least one additional suturing device.

13. An apparatus according to claim 12, wherein said anchoring devices are set apart a predetermined distance so that one anchoring device is used on one side of said deep incision or wound through the abdominal fascia and said other anchoring device is used on an opposite side of said deep incision or wound.

14. An apparatus according to claim 13, wherein said anchoring devices are oblong-shaped plate anchoring devices connected to said suturing line of said suturing device.

15. An apparatus according to claim 14, wherein said oblong-shaped anchoring devices are oblong-shaped plate anchoring devices connected to said suturing line of said suturing device in a manner to allow said oblong-shaped anchoring devices to be aligned with a length of said suturing device when loaded within said suturing device delivery passageway of said hollow needle device, and then aligned transversely relative to said suturing device after insertion through the tissue surrounding the deep incision or wound to anchor said suturing device.

16. An apparatus according to claim 8, wherein said anchoring devices are oblong rod-shaped anchoring devices connected to a suturing line of said suturing device.

17. An apparatus according to claim 16, wherein said oblong rod-shaped anchoring devices are provided with a throughhole for connecting with a suturing line of said suturing device.

18. An apparatus according to claim 17, wherein said oblong rod-shaped anchoring devices are provided with at least one groove for accommodating said suturing line when said oblong rod-shaped anchoring devices are aligned with a length of said suturing device.

19. A method of suturing tissue surrounding a deep incision or wound through the abdominal fascia, said method comprising the steps of:

making a set of penetrating holes on opposites sides of the deep incision or wound through the abdominal fascia with a hollow needle;

inserting a suturing device through each penetrating hole in the abdominal fascia, said suturing device including multiple anchoring devices having through holes and a suturing line passing through said through holes of said anchoring devices to connect the suturing line to the anchoring devices;

anchoring said suturing device in said penetrating holes in the abdominal fascia, and tightening said suturing device to pull said penetrating holes in the abdominal fascia together to close the deep incision or wound.

20. A method of suturing tissue surrounding a deep incision or wound through the abdominal fascia, said method comprising the steps of:

making a set of penetrating holes on opposites sides of the deep incision or wound through the abdominal fascia with a hollow needle device;

inserting separate suturing devices through each penetrating hole through the abdominal fascia, said suturing device including multiple anchoring devices having through holes and a suturing line passing through said through holes of said anchoring devices to connect the suturing line to the anchoring devices;

anchoring said suturing devices in said penetrating holes through the abdominal fascia; and tying said suturing devices together to pull said penetrating holes though the abdominal fascia together to close the deep incision or wound.

21. An apparatus according to claim 1, including a suture loading device provided with a loop portion, said loop portion of said suture loading device configured to be inserted through said needle so that said loop portion extends beyond said cutting tip portion of said hollow needle device whereby a suture can be threaded through said loop portion and then said suture loading device can be withdrawn from said hollow needle device to load the suturing device within said suturing device delivery passageway of said needle readied for insertion through the abdominal fascia.

* * * * *